United States Patent
Snyder et al.

(10) Patent No.: US 9,263,043 B2
(45) Date of Patent: Feb. 16, 2016

(54) STUTTERING INHIBITION METHOD AND DEVICE

(75) Inventors: Gregory John Snyder, Oxford, MS (US); Dwight E. Waddell, II, Oxford, MS (US); Paul Mallette Goggans, Oxford, MS (US)

(73) Assignee: UNIVERSITY OF MISSISSIPPI, University, MS (US)

( * ) Notice: Subject to any disclaimer, the term of this patent is extended or adjusted under 35 U.S.C. 154(b) by 0 days.

(21) Appl. No.: 13/513,733

(22) PCT Filed: Dec. 3, 2010

(86) PCT No.: PCT/US2010/058945
§ 371 (c)(1),
(2), (4) Date: Jun. 4, 2012

(87) PCT Pub. No.: WO2011/069095
PCT Pub. Date: Jun. 9, 2011

(65) Prior Publication Data
US 2012/0289766 A1 Nov. 15, 2012

Related U.S. Application Data

(60) Provisional application No. 61/266,866, filed on Dec. 4, 2009.

(51) Int. Cl.
*A61F 5/58* (2006.01)
*G10L 15/24* (2013.01)
*G10L 21/06* (2013.01)
*G10L 21/057* (2013.01)

(52) U.S. Cl.
CPC . *G10L 15/24* (2013.01); *A61F 5/58* (2013.01); *G10L 21/06* (2013.01); *G10L 2021/0575* (2013.01)

(58) Field of Classification Search
CPC .................................. A61F 5/58; G09B 19/04
USPC .............. 600/23; 434/112, 116, 185; 704/271
See application file for complete search history.

(56) References Cited

U.S. PATENT DOCUMENTS

| | | | | |
|---|---|---|---|---|
| 4,685,448 A | * | 8/1987 | Shames et al. | 600/23 |
| 4,784,115 A | * | 11/1988 | Webster | 600/24 |
| 6,231,500 B1 | | 5/2001 | Kehoe | |
| 2006/0064037 A1 | * | 3/2006 | Shalon | A61B 5/0006 600/586 |
| 2006/0183964 A1 | * | 8/2006 | Kehoe | 600/23 |
| 2006/0190056 A1 | * | 8/2006 | Fowler et al. | 607/45 |
| 2007/0010704 A1 | * | 1/2007 | Pitulia | 600/23 |
| 2009/0105785 A1 | | 4/2009 | Wei et al. | |
| 2009/0264789 A1 | * | 10/2009 | Molnar et al. | 600/544 |
| 2011/0021320 A1 | * | 1/2011 | Lenhardt | 482/9 |

FOREIGN PATENT DOCUMENTS

| | | | |
|---|---|---|---|
| JP | 2000166962 A | | 6/2000 |
| JP | 2001183973 A | | 7/2001 |
| JP | 2002040927 A | | 2/2002 |
| WO | WO 2007005582 A1 | * | 1/2007 |

* cited by examiner

*Primary Examiner* — Charles A Marmor, II
*Assistant Examiner* — Thaddeus Cox
(74) *Attorney, Agent, or Firm* — Butler Snow LLP

(57) ABSTRACT

A method and device is disclosed for reducing and controlling stuttering. The method involves tactile feedback of the stutterer's own speech to reducing stuttering. In one embodiment, the device may detect speech by audible or mechanical means, and the feedback may be produced by vibration mechanisms.

20 Claims, 9 Drawing Sheets

STUTTERING INHIBITION METHOD AND DEVICE

CROSS-REFERENCE TO RELATED APPLICATIONS

This application claims priority to U.S. provisional application 61/266,866 filed Dec. 4, 2009, hereby incorporated by reference.

FIELD OF THE INVENTION

The present invention is generally directed toward a method of controlling and reducing stuttering. It is further directed toward a device that encompasses the claimed method of reducing stuttering.

BACKGROUND OF THE INVENTION

Persistent developmental stuttering is a speech disorder that affects approximately 1% of the world's population and is easily recognizable by its hallmark characteristics of: whole-word repetitions, part-word repetitions, syllable prolongations, or the inability to get the sound or syllable out at all (inaudible postural fixations). While the symptoms of stuttering are well-known, the etiology is not. Without a clear understanding of what causes stuttering, the treatments for stuttering are limited. Consequently, there are no valid cures for the pathology, and the best available speech treatments of the prior art only allow for a limited amount of control over stuttered speech. Subsequently, the inability to successfully control (or eliminate) stuttering produces negative consequences of life-altering significance. In short, the inability to orally communicate in a socially acceptable fashion has the potential to drastically reduce professional, social and educational opportunities.

It has been shown that the incidence of stuttering can be reduced by using a second speech signal via speech feedback. Stuttering was reduced by having a stutterer speak in choral unison with another speaker. Technology allows us to mimic this effect, with Delayed Auditory Feedback (DAF) or Frequency Altered Feedback (FAF). The principles of DAF/FAF can be delineated into three simple stages: (1) a microphone captures the speaker's speech signal; (2) this speech signal is then digitally processed, where an adjustable delay is added to the signal (50 ms to 200 ms) and/or the frequencies in the speech signal are shifted higher or lower; (3) this altered speech signal is then re-introduced to the speaker via headphones. A variety of DAF/FAF devices are already on the market; however, they are expensive and distracting to use. These DAF/FAF devices suffer from many problems. For example, they have a poor signal to noise ratio. Additionally, the earphones interfere with hearing the surrounding environment. Visual speech feedback has also been shown to significantly enhance fluency via visual choral speech or delayed visual feedback; however, this methodology is not amenable to prosthetic implementation due to cost form and factor.

Treatments such as auditory feedback and visual feedback have proven to be effective but have the downside of being either audibly or visually distracting. Prosthetics based on these treatment methodologies are annoying to the user, they impede hearing and negatively affect dynamic conversation, and the signal to noise ratio is often almost unacceptably low. There exists a need for a method and device that can effectively reduce stuttering without the problems exhibited by the visual and auditory feedback methods.

SUMMARY OF THE INVENTION

A novel method for controlling and reducing stuttering is disclosed, along with a device that incorporates the method.

The disclosed method comprises of the steps of detecting vocalization and providing tactile feedback to the user. Vocalization may be detected by detecting an auditory speech signal (for example, by using a microphone), or by detecting a vibrotactile speech signal by using an accelerometer or vibration sensing device. The tactile feedback is then created by a vibration producing mechanism.

The claimed device is a prosthetic that implements the principle of tactile feedback to reduce stuttering. This device is capable of capturing the speech of the user, transmitting it to a processing unit, and converting it to a corresponding output in the form of vibrations. Input to this device is a person's speech. Output from this device is a corresponding mechanical vibration that one can sense through their skin.

BRIEF DESCRIPTION OF THE DRAWINGS

Further advantages of the invention will become apparent by reference to the detailed description of preferred embodiments when considered in conjunction with the drawings.

DETAILED DESCRIPTION

The following detailed description is presented to enable any person skilled in the art to make and use the invention. For purposes of explanation, specific details are set forth to provide a thorough understanding of the present invention. However, it will be apparent to one skilled in the art that these specific details are not required to practice the invention. Descriptions of specific applications are provided only as representative examples. Various modifications to the preferred embodiments will be readily apparent to one skilled in the art, and the general principles defined herein may be applied to other embodiments and applications without departing from the scope of the invention. The present invention is not intended to be limited to the embodiments shown, but is to be accorded the widest possible scope consistent with the principles and features disclosed herein.

The claimed method for reducing stuttering involves two basic steps: inputting of a signal corresponding to speech and outputting of a corresponding vibrotactile feedback. The claimed device incorporates these steps into a portable device.

In a preferred embodiment, the vibrotactile feedback is speech activated, or triggered by a push-button or other activation switch in cases of a silent stutter. Any device that can detect speech can be used in the methods for inputting the speech signals. Suggested methodologies for capturing speech include the use of a throat-microphone or Bluetooth headset for detecting audible sounds, or the use of sensors such as accelerometers or vibrations-sensing devices. The signal input device should be able to sense and relay the speech signal or its intensity to the signal output device in real time. Additionally, circuitry or filters would be needed to reduce inappropriate activation of the device due to background noise or incidental movement.

The signal output device would give the stutterer a vibrating source that is speech-activated via the signal input. In a preferred embodiment, the vibrating source has some type of gain to control the intensity of the vibration, and means to alter the frequency content. Ideally, the vibrating source should also have sufficient temporal resolution, such that users can sense the boundaries of syllables, words and phrases. Additional signal processing such as temporal delays or frequency shifting may be performed on the input signal to create varying effects on the tactile feedback.

Figure 1:
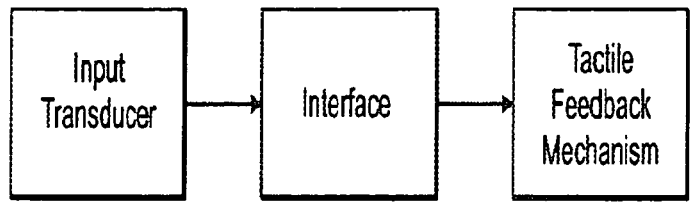
FIG. 1 depicts a block diagram of the overall design of the device.

A block diagram of the basic design incorporating the steps of the claimed method is shown in FIG. 1. The first component of the device is an input transducer. Its purpose is to sense the speech of a user and, in some way, produce a corresponding electrical signal. Input transducers can include any device that can convert sound or mechanical energy into electrical energy, including microphones (including noise-cancelling and throat microphones), accelerometers, or vibration sensors.

A second component is the vibrating mechanism, also referred to herein as the tactile feedback mechanism. The purpose of this element is to take an electrical signal and convert it to a mechanical vibration. The vibrations emitted by the vibrating mechanism should coincide with the electrical signal that is its input, including frequency and amplitude response. The vibrating mechanism can include speakers, shakers, and motors.

Functionally, a third component of the device is the interface between the first two elements discussed. The input to this component is the electrical signal from the input transducer, and the output of this component is the electrical signal that is fed to the vibrating mechanism. The interface additionally serves to remove unwanted background noise and provide signal processing.

It should be appreciated that the device is portable, such that it can easily be carried in the user's pocket. All circuitry would be housed in a sturdy housing with leads running from the input to the main interface, and an output wire running to the tactile feedback mechanism. The device is not to be limited to versions that require wires and leads. A wireless version is contemplated to be within the scope of the invention and would be effective in reducing stuttering.

WORKING EXAMPLES

Two embodiments of the claimed device are described below to enable a person skilled in the art to make and use the invention. The two embodiments share the same power supply and vibrating mechanism for providing tactile feedback.

Any power source for the device may be used in implementing the device, including AC or DC power. For the two embodiments, the main power source is a combination of two 9V batteries. The use of batteries allows for a stable source of steady current from a mobile source. Although the input devices of our embodiments (microphone and accelerometer) only require positive voltages, our operational amplifiers required negative voltage supplies. For this, a voltage divider circuit was used. This circuit uses two 9V batteries in series and divides the total of 18 volts into equal halves with the help of two equal, large-valued resistors. Connecting the ground of the circuit between the two resistors will result in the negative voltage relative to the ground point. With this point as 0 voltage point, the point connected to the negative end of the batteries in series would give the negative half of the divided voltage. Each resistor is in parallel with a small valued capacitor to improve the supply's noise immunity. The circuit also incorporates an on-off switch. The switch opens up the loop containing batteries in the circuit so as to cut off the power supply and put the device in an inactive state.

In addition, the device can have a push button, or other electric switch, that causes the skin stimulator to vibrate at a fixed frequency. This is particularly useful when the user is having a silent moment of stuttering. It likely can also be used to assist other motor initiation disorders, such as moments of gate freezing associated with Parkinson's disease patients.

Any device that produces a tactile output that can be felt by the person wearing the device can be used in the claimed method. In the disclosed embodiments, vibration producing mechanisms were used as the output of the tactile feedback device. The input signal may be processed by the circuitry in the interface to adapt for various users before outputting to the vibration mechanism. A specialized skin transducer called a "Skin Stimulator," (manufactured by Audiological Engineering Corp. Somerville, Mass, model VBW32) was selected as the vibration producing mechanism. This product operates very similarly to a dynamic speaker, except that its purpose is directed toward outputting mechanical vibrations instead of sound. The input to the vibrating mechanism is an electrical signal. The same Skin Stimulator has been used in other applications. For example, its use is described in U.S. Pat. No. 5,035,241 for tactile stimulation of deaf individuals (hereby incorporated by reference). The physical and electrical specifications of the Skin Stimulator are listed below:

Size: 1" long×0.73" wide×0.42" thick
Weight: 6.5 grams
Coil resistance: 32 ohms
Frequency: 250 Hz nominal peak
Usable output (at reduced levels): 100 Hz to 800 Hz
Amplitude range: sensory threshold to 50 dB above threshold
Transient response: 5 milliseconds (attack and decay)
Power consumption: 200 milliwatts typical at 100% duty cycle
Nominal voltage drive: 2.5 Vrms The vibrating mechanism could be hand held, or it may be attached to any part of the body with double sided tape. For example, it is contemplated that the vibrating mechanism could be worn on the wrist with a wrist strap so that it looks like a watch. Alternatively, it may be attached to the body with an adhesive, such as double-side tape Working Example Embodiment 1

Figure 2:
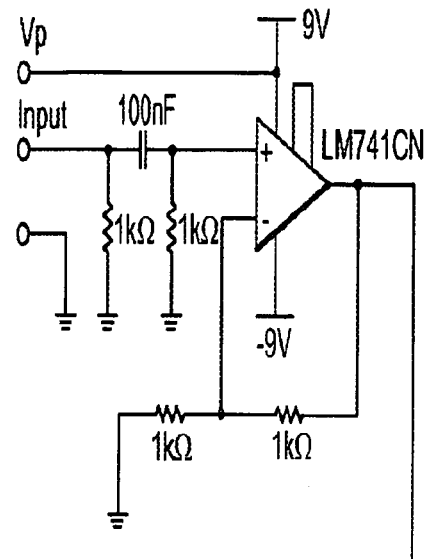
FIG. 2 shows a full circuit schematic of the first embodiment.
Figure 2:
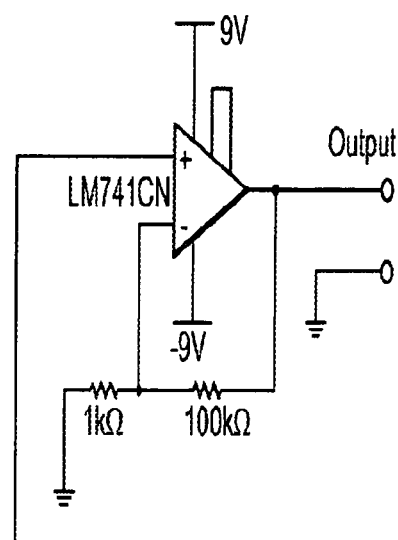
Figure 2:
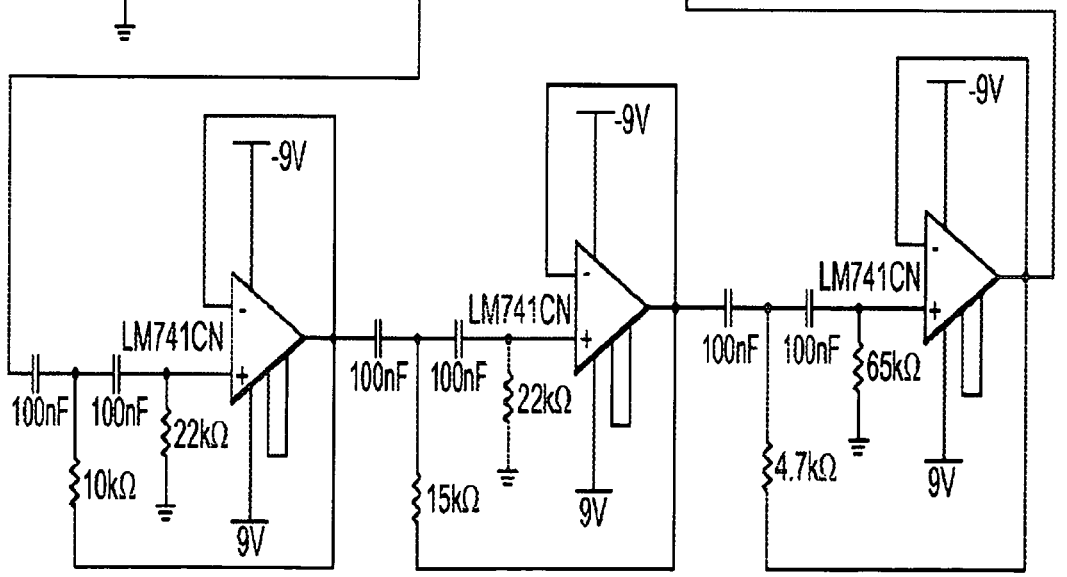

A full circuit schematic of the first embodiment can be viewed in FIG. 2.

The first embodiment captures the vocal cord vibrations of the user, converts them to an electrical signal, and drives the vibrating device corresponding to the electric signal. To accomplish this, we used an accelerometer as the input device which would be attached on the user's throat. The signal from the accelerometer is sent through an active high-pass filter and amplified to feed it to the vibrating device. The high pass filter removes unwanted lower frequency signals due to the user's movement. A low pass filter was not incorporated with this first embodiment since higher frequency vibrations out of the vibrating device cannot be felt by the user; hence a significant impact on the feedback characteristics is not created.

This first embodiment uses an ACH-01-03/10 accelerometer (manufactured by Measurement Specialties, Inc. Hampton, Va.) as its input device. The reason for selecting an accelerometer as an input device is to capture the vibrations of the speaker's throat and convert them to an electrical signal. This specific accelerometer was selected mainly because of its frequency and phase response range. It has almost constant frequency and phase responses from 20 Hz-20 KHz which cover the main range of fundamental frequencies that this device will measure due to produced speech. Another reason for selecting this specific accelerometer is because it is designed for general purpose, and its dimensions are practical enough to be mounted on the speaker's throat.

The accelerometer uses a piezoelectric film as a transducer coupled with a JFET. The JFET accepts the power supply, and the piezoelectric transducer acts as the controller to control how much signal needs to be sent as an output through the JFET, depending upon the acceleration experienced by the transducer.

This accelerometer requires a factory recommended pre-amplifier circuit to operate. The amplifier is a non-inverting amplifier with a DC-blocking capacitor that allows only the AC output signal of the accelerometer to pass. Since the type of operational amplifier is not critical, we used the LM741 operational amplifier (manufactured by National Semiconductor, Santa Clara, Calif.) for simulation and illustration purposes, however, any suitable general purpose operational amplifier could be used. The gain of the amplifier can be calculated as follows:

Voltage Gain=90kΩ/10$k$Ω=9

When designing the first embodiment, an accelerometer is used as the input device. The accelerometer is a device used to measure vocal as well as movement artifact induced accelerations. With the first embodiment, the accelerometer is used to capture the vibrations of the vocal chords. As the range of human voice is from approximately 90 Hz to 1 kHz, a filter is used to block frequencies lower than the range of the human voice. This high pass filter is helpful in preventing the device from responding to the user's every movement, only responding to the user's vocal input vibrations.

Figure 4:
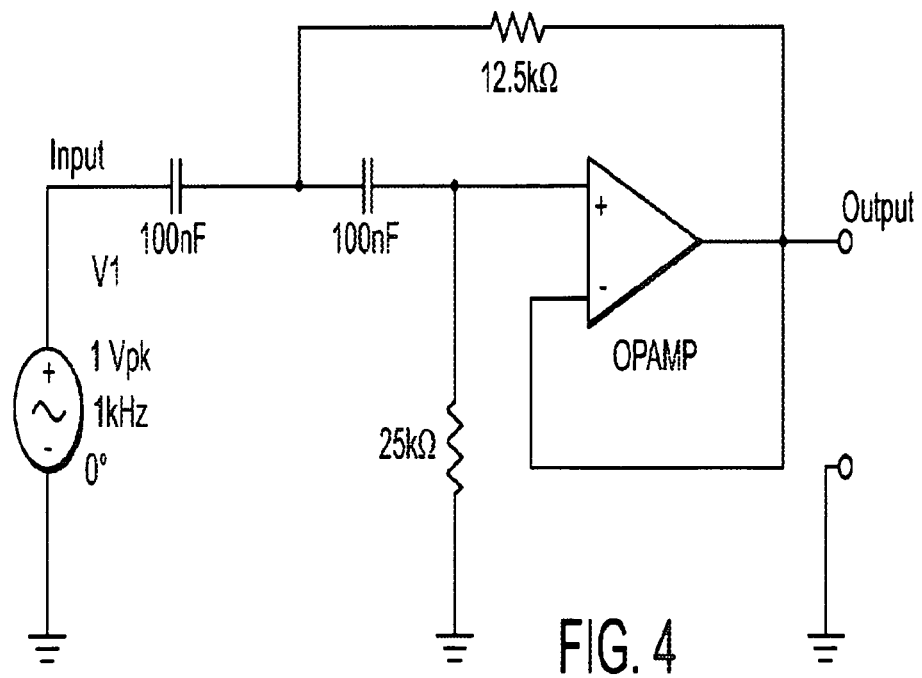
FIG. 4 depicts a $2^{nd}$ order Sallen Key filter with unity gain.
Figure 5:
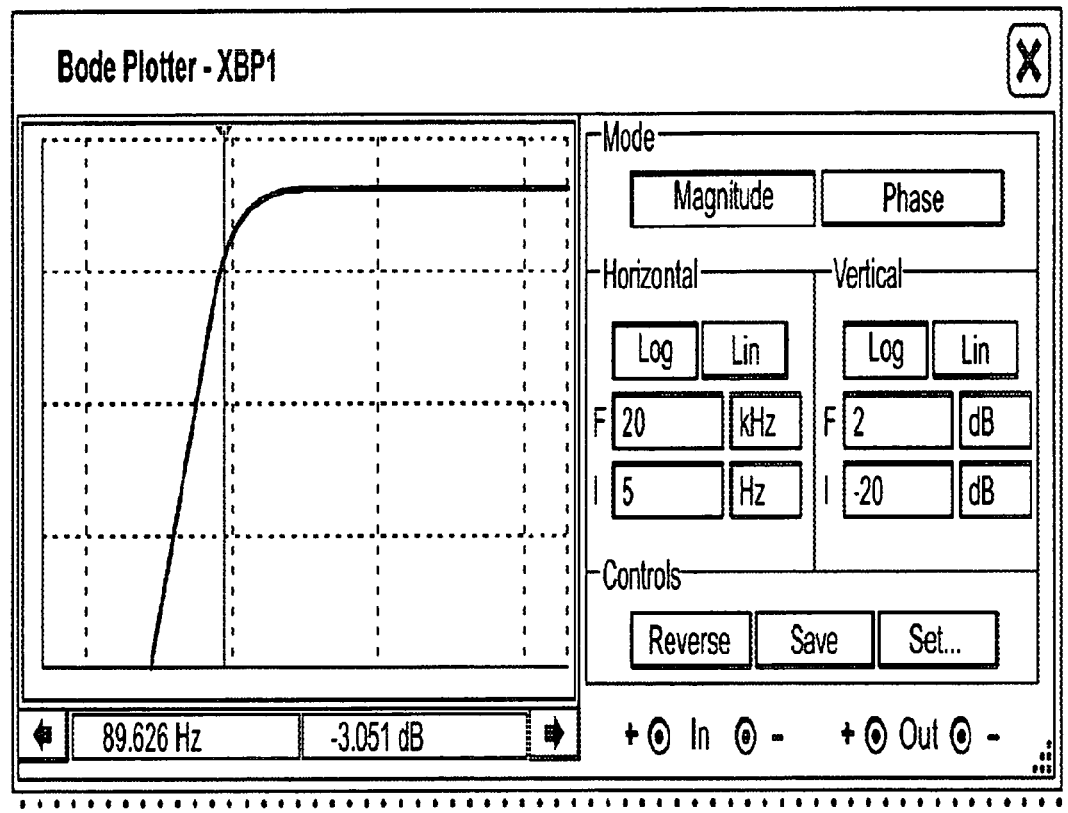
FIG. 5 shows a plot of the magnitude response of a $2^{nd}$ order Sallen-Key High Pass filter.

With the first embodiment, a second-order Sallen-Key High Pass filter is used. The Sallen-Key design is both simple and cost effective, using only one operational amplifier and two generic resistors and capacitors. FIG. 4 depicts a second-order Sallen-Key filter with unity gain designed to cut off frequencies below 90 Hz, and FIG. 5 shows its magnitude response, both realized using MULTISIM 10 circuit design software (National Instruments, Austin, Tex.). Resistor values have been slightly adjusted to standard available values.

In order to improve the magnitude response of the filter, the filter order is raised by cascading two additional Sallen-Key stages into the design. This sixth-order Sallen-Key High Pass filter yields a much sharper response, cutting off unwanted frequencies much faster.

Figure 6:
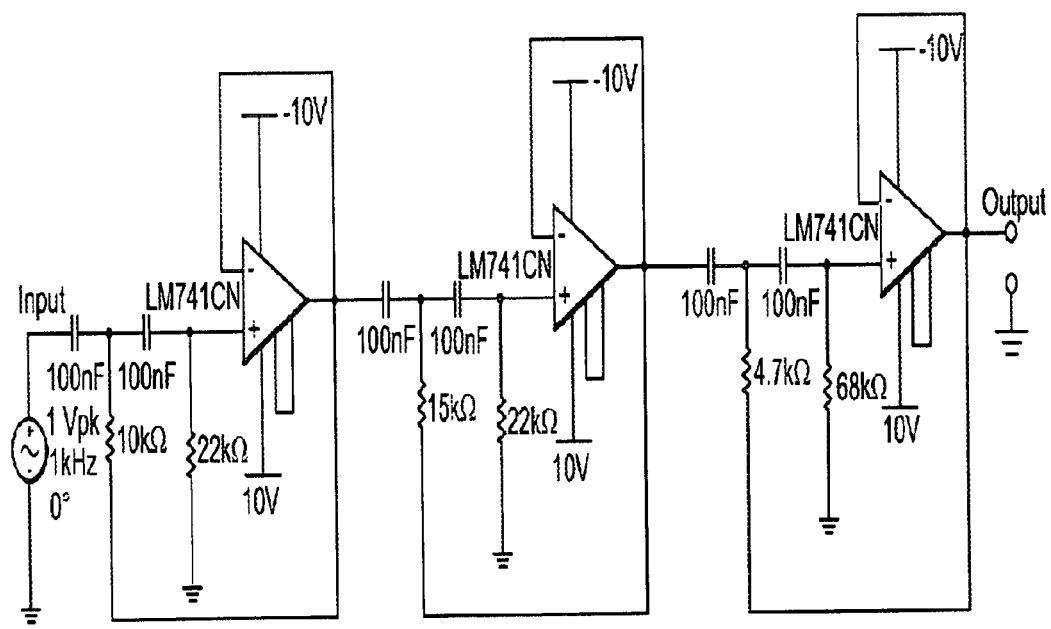
FIG. 6: shows a $6^{th}$ order High Pass Filter for the Accelerometer design.
Figure 7:
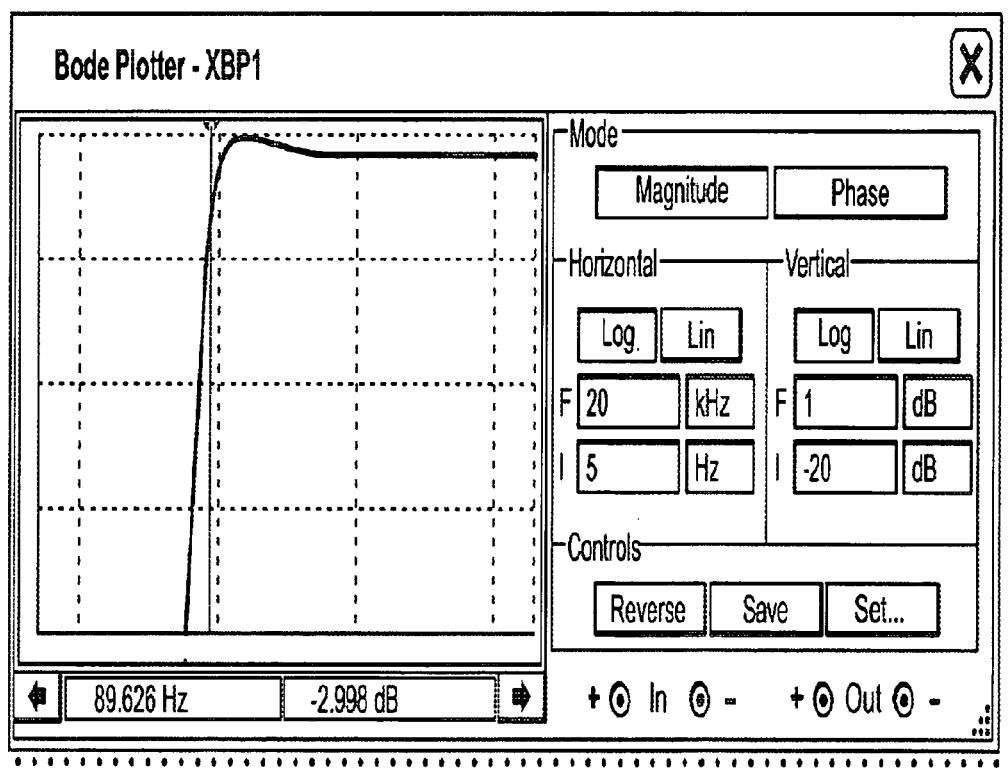
FIG. 7 shows a plot of a magnitude response for a 3-stage Sallen-Key High Pass.

The 3-Stage Sallen-Key High Pass Butterworth filter is shown in FIG. 6. Resistor values have been adjusted slightly to standard available values. Its magnitude response is shown in FIG. 7. The −3 dB frequency, also known as the cutoff, is traced at approximately 90 Hz. This frequency is the desired cutoff point for the accelerometer for this embodiment.

Figure 8:
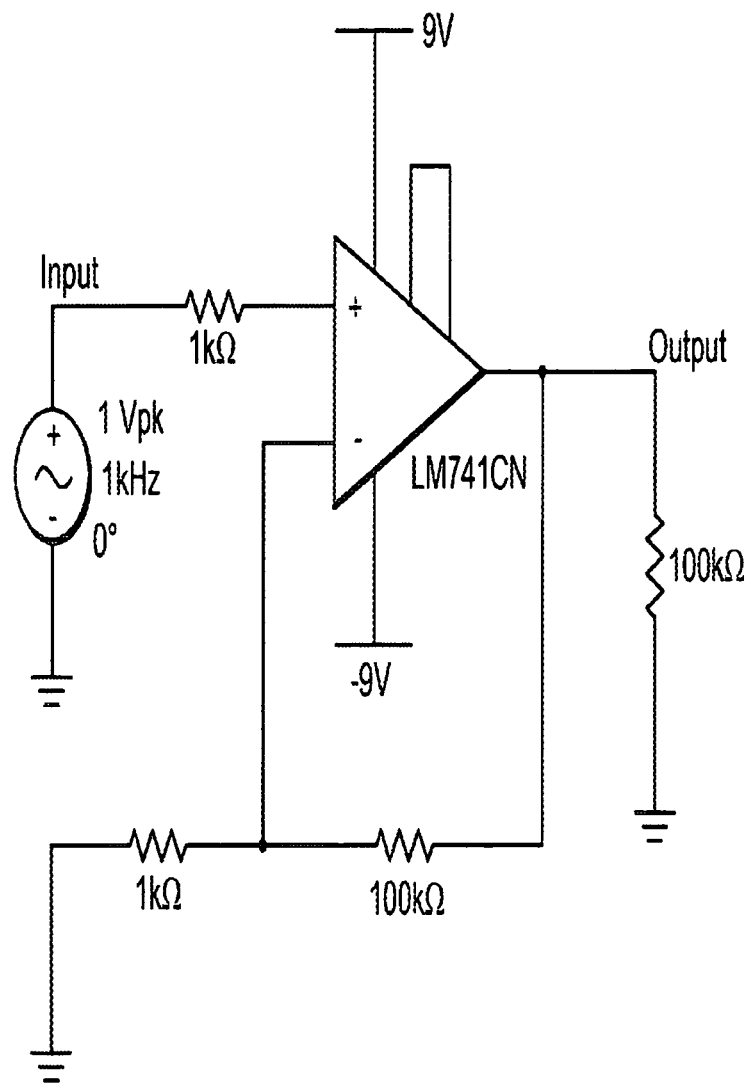
FIG. 8 shows an Amplifier Circuit as described in relation to the first embodiment.

The main purpose of having an amplifier after the high pass filter is to boost the filtered signal from the accelerometer before sending it to the output device. In order to make the output device vibrate to a desired level, the signal needs to be amplified to as high as 18V peak-to-peak (Vpp). This amplifier is also a non-inverting amplifier with a gain of 100. The schematic diagram of the amplifier is shown in FIG. 8. This uses an LM741 operational amplifier for illustration and modeling purposes. In reality, our embodiment uses one of the operational amplifiers in the LM324 Quad Op-Amp chip that we also used for our high pass filter. The reason for using this amplifier is to save space since the circuit needs to be compact enough to fit inside a small case for portability.

The user of this first embodiment would place the accelerometer against his throat so that the accelerometer could sense the vocal vibrations as he speaks. The accelerometer sends the corresponding electrical signal to the interface, where it may be further processed. The interface would then send a corresponding electrical output to the Skin Stimulator worn at another part of the user's body, such as the finger. Effectively, the user would have tactile feedback at his finger of the vocal vibrations that are happening at his throat.

Working Example

Embodiment 2

Figure 3:
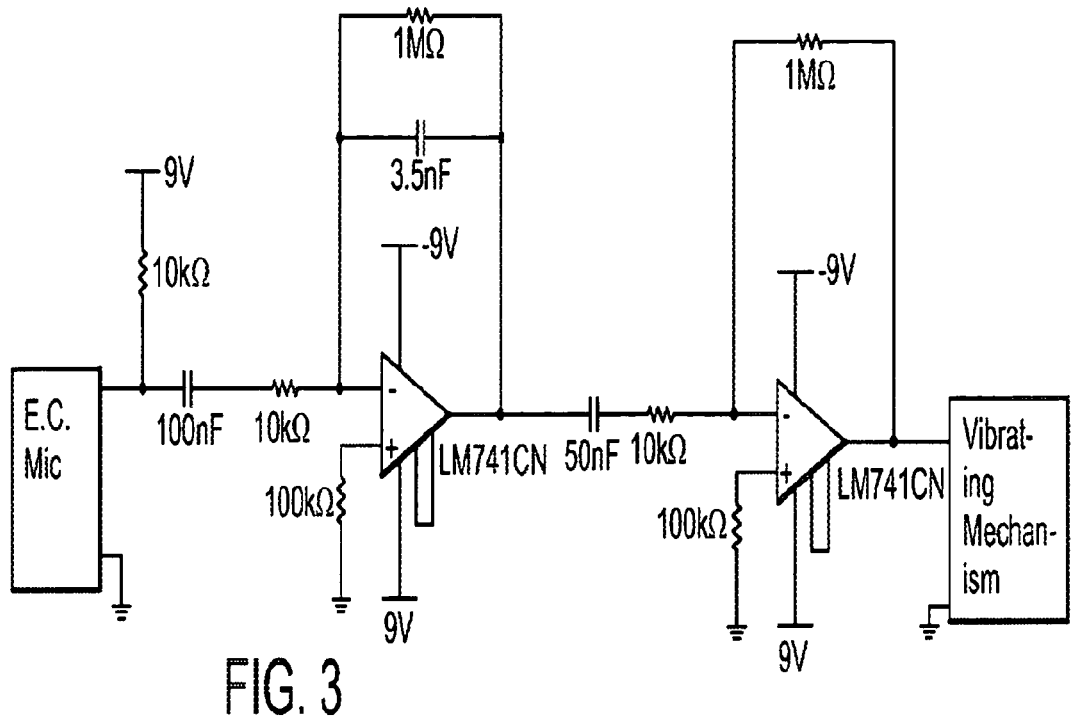
FIG. 3 depicts a circuit diagram of the second embodiment.

A complete schematic of the second embodiment can be viewed in FIG. 3. The components of the second embodiment are individually introduced and explained in the following paragraphs.

The second design uses an electret condenser microphone to produce the input signal. The microphone is essentially a capacitor with one fixed plate. The position of the other plate of the capacitor varies depending on the pressure of the sound waves coming into contact with it. Capacitance varies according to the change in distance between the two plates. The charge on the plates is nearly constant; therefore, the voltage across the capacitor must also vary with respect to the pressure waves. It is this voltage that is the output of the microphone. A capacitor is used to block the DC bias voltage from the output. The bias resistor that connects the microphone's positive lead to the source voltage is 10 kΩ as specified by the manufacturer's data sheet for the microphone. This value can be slightly adjusted. Doing so will adjust the output gain of the microphone. A simple electret condenser microphone was used for initial testing of this design, but a "noise-cancelling" microphone is preferable to remove unwanted environmental noise.

The selected microphone has a reasonably constant frequency response from 20 Hz-15 KHz which cover the main range of fundamental frequencies that this device will measure due to produced speech.

Figure 9:
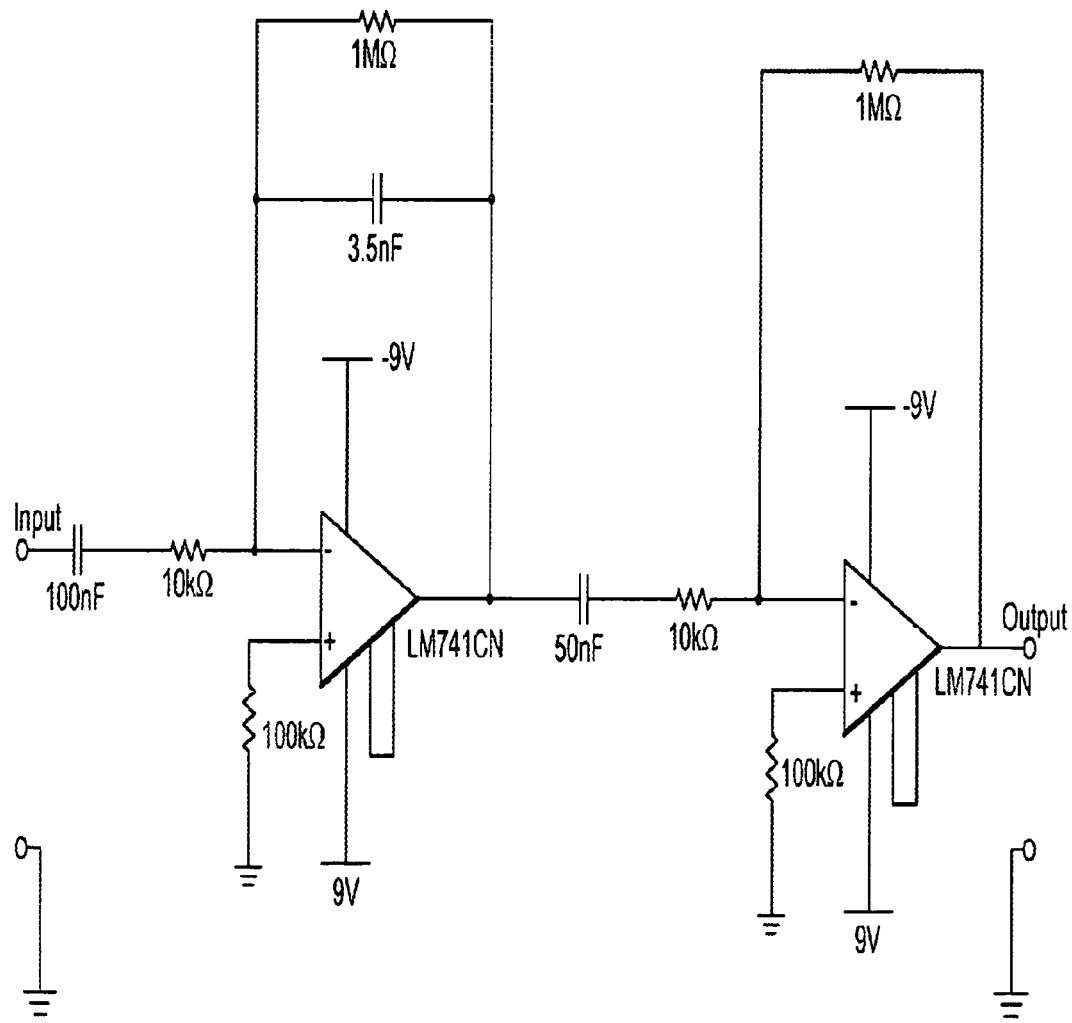
FIG. 9 is an interface two stage amplifier used in the second embodiment.

The interface for this embodiment's design consists of a two stage amplifier. The input signal from the microphone is around the range of 20 mV peak. The output voltage needed should be close to 9V peak for optimal operation of the output device. It should be noted that any output voltage that exceeds 9V peak will, in fact, be clipped at 9V. This is because the source voltage used to power the operational amplifiers has been established at 9V, and the output cannot possibly surpass this. Consequently, this interface needs to produce a substantial amount of gain. The interface design is shown in FIG. 9.

The interface needs to be able to produce adequate gain and, if possible, perform at its optimum ability for the fundamental frequencies. The 100 nF capacitor at the input is the DC blocking capacitor used at the output of the electret condenser microphone. The feedback loop contains a 1 MΩ resistor in parallel with a 3.5 nF capacitor. This parallel combination is a first order low pass filter which suppresses the gain of frequencies higher than the fundamental frequency range. The gain of the first stage of the amplifier is set by the ratio of the feedback impedance to the input impedance of the inverting input to the operational amplifier.

The output of the first stage is fed to the input of the second stage. The input of the second stage consists of a series combination of a 50 nF capacitor and a 10 kΩ resistor. This series combination is a high pass circuit (similar to the input of the first stage). The capacitor blocks any DC signal components and also suppresses the gain of frequencies lower than the fundamental frequencies. The gain of this stage is approximately the ratio of the feedback resistor and the input resistor. The following equation shows the calculation of gain for this stage:

Voltage Gain=1000 kΩ/10 kΩ=100=20 dB

Figure 10:
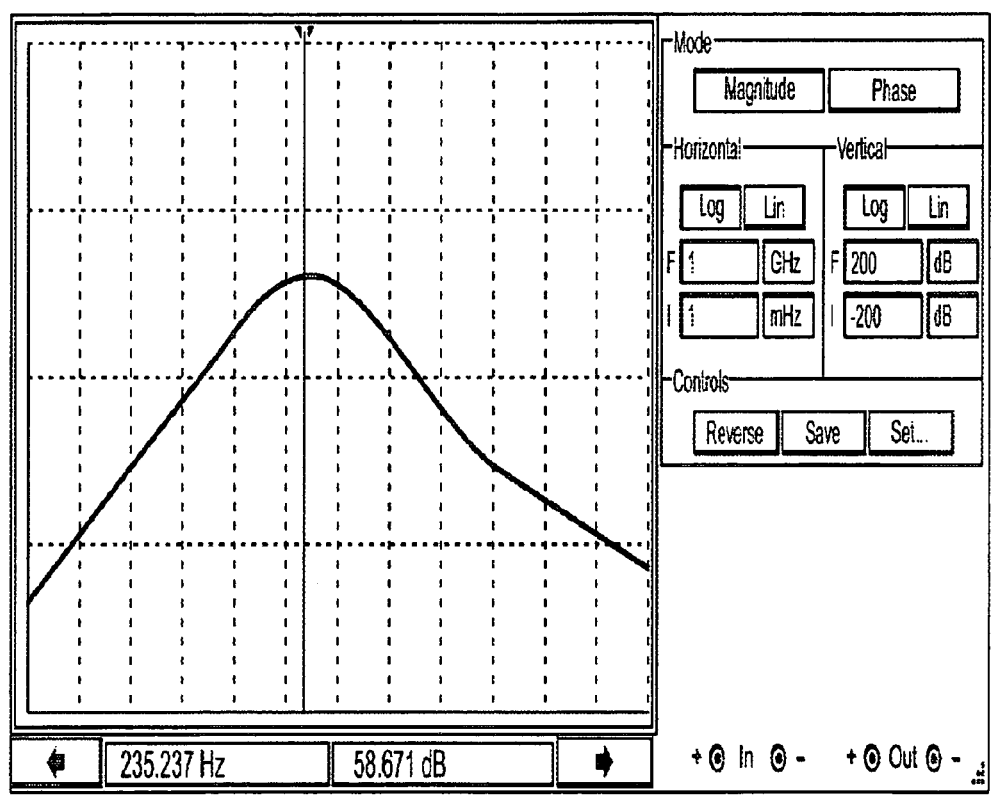
FIG. 10 shows a Bode plot of the frequency response for interface of the second embodiment.

FIG. 10 is a Bode plot from the MULTISIM circuit design software of the frequency response of the design. The maximum of the curve lies between the horizontal division that represents the range of 100 Hz to 1 kHz. The maximum is around 250 Hz which coincides with the resonant frequency of the output device.

The user of this second embodiment would place the electret microphone within range of his voice so that microphone could sense his speech. The microphone sends the corresponding electrical signal to the interface, where it may be further processed. The interface would then send a corresponding electrical output to the Skin Stimulator worn somewhere on the body, such as on a finger. Effectively, the user would have tactile feedback of his voice at his fingers as he speaks.

Clinical Results.

Figure 11:
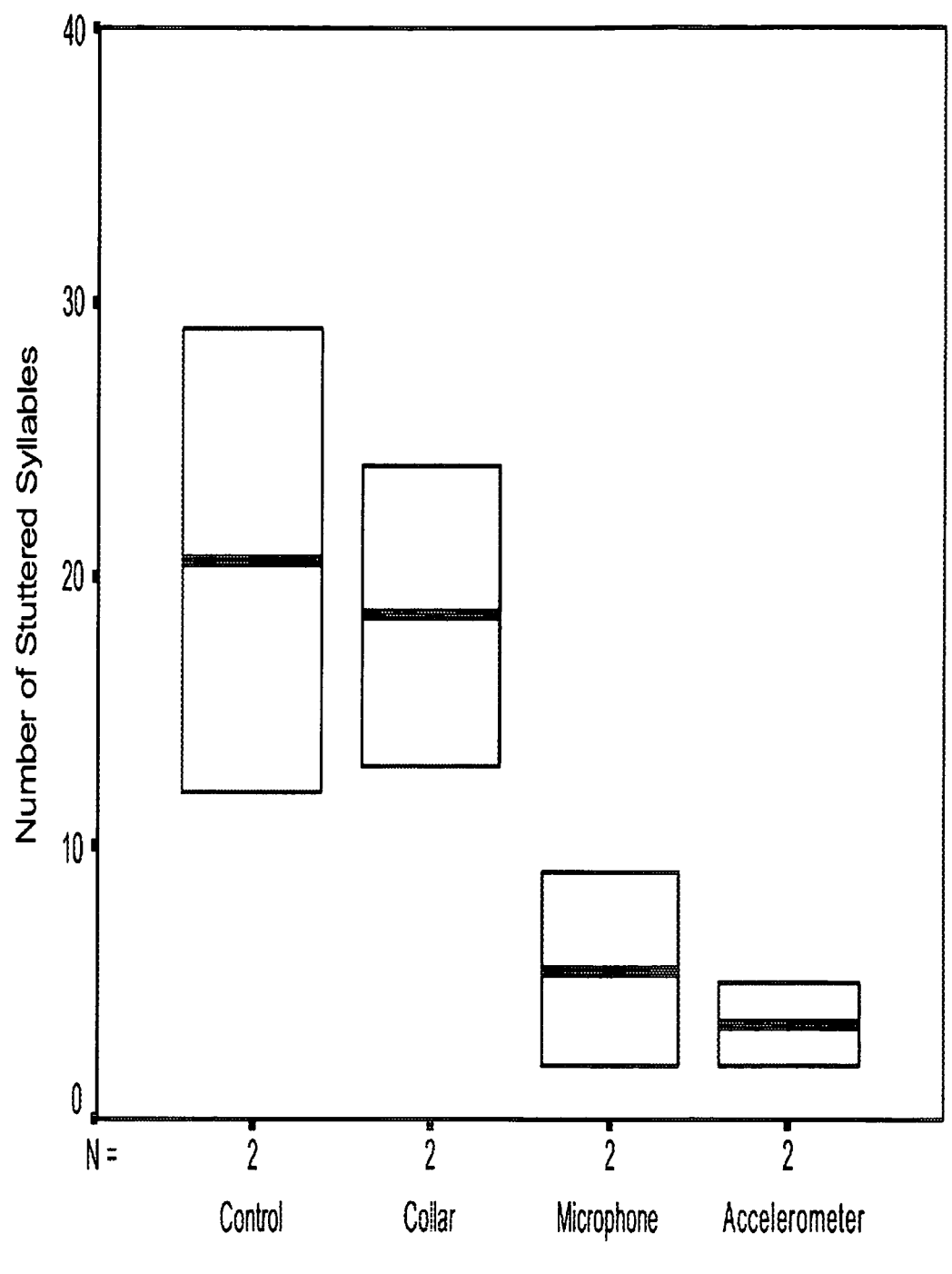
FIG. 11 is a box plot of the results of clinical experiments.

The disclosed devices were tested to determine their efficacy in reducing stuttering. The results are depicted in the box plot of FIG. 11. The X axis of this box plot shows the speaking conditions. The speaking conditions include a control condition, a "collar" condition (where the participant spoke with the sensory-input collar on their neck, but not active), a "microphone" condition (where the method of sensory input was the microphone), and an "accelerometer" condition (where the method of sensory input was the accelerometer).

The Y axis is the frequency of stuttered syllables out of 300 syllable reading passages.

The descriptive statistics of the raw data can be seen in Table 1 below. It shows the average number of stuttered syllables (out of 300 syllables) for each speaking condition. (Standard deviation is also included.)

TABLE 1

Descriptive Statistics

| | Mean | Std. Deviation | N |
| --- | --- | --- | --- |
| CONTROL | 20.5000 | 12.02082 | 2 |
| COLLAR | 18.5000 | 7.77817 | 2 |
| MIC | 5.5000 | 4.94975 | 2 |
| ACCELEROMETER | 3.5000 | 2.12132 | 2 |

The standard deviation is large relative to the mean. This is common in small sampled stuttering research. One participant was quite severe; the other was relatively mild. Therefore, the difference in overall severity plays havoc on the statistics a bit. However, the trend is still quite obvious: not only does tactile feedback reduce the number of stuttered syllables, but it also reduces the variability of stuttered syllables, as well. Furthermore, this finding was consistent over different levels of severity.

Raw (non-transformed) data was also obtained from a Repeated Measures Analysis of Variance, and is shown in Table 2:

TABLE 2

Tests of Within-Subjects Effects

| | Source | Type III Sum of Squares | df | Mean Square | F | Sig. | Partial Eta Squared | Noncent. Parameter | Observed Power(a) |
| --- | --- | --- | --- | --- | --- | --- | --- | --- | --- |
| TACTILE | Sphericity Assumed | 458.000 | 3 | 152.667 | 8.561 | .056 | .895 | 25.682 | .593 |
| | Greenhouse-Geisser | 458.000 | 1.000 | 458.000 | 8.561 | .210 | .895 | 8.561 | .182 |
| | Huynh-Feldt | 458.000 | . | . | . | . | .895 | . | . |
| | Lower-bound | 458.000 | 1.000 | 458.000 | 8.561 | .210 | .895 | 8.561 | .182 |
| Error (TACTILE) | Sphericity Assumed | 53.500 | 3 | 17.833 | | | | | |
| | Greenhouse-Geisser | 53.500 | 1.000 | 53.500 | | | | | |
| | Huynh-Feldt | 53.500 | . | . | | | | | |
| | Lower-bound | 53.500 | 1.000 | 53.500 | | | | | |

(a)Computed using alpha = .05

The following observations from this data are notable: (a) The F statistic is a relatively low 8.561. (b) The probability of error is 0.056, which approaches the arbitrary "statistical significance" and is quite reliable and consistent. (c) The effect size, represented by the partial eta squared, is 0.895—indicating that the reduction in stuttered syllables is quite large. The data shows that we have a relatively consistent finding of a very large change in stuttering frequency.

The problem with this analysis is that the participants were of different severities of stuttering—one rather severe, the other quite mild. The differential severities reduce statistical power. In other words, it makes the test less sensitive to detect a significant change in stuttering frequency from random variation in stuttered speech. This problem is well-known and documented in the stuttering literature. One common way to combat this problem is to normalize the data by taking a square-root transformation. In other words, take the square root of all of the numbers of stuttered syllables. This tightens up the data's variance; in effect, this reduces the overall stuttering severity differential that each participant demonstrated relative to each other. Table 3 shows the same exact Repeated Measure Analysis of Variance, but on the transformed data (square root transformation).

TABLE 3

Tests of Within-Subjects Effects

| Source | | Type III Sum of Squares | df | Mean Square | F | Sig. | Partial Eta Squared | Noncent. Parameter | Observed Power(a) |
|---|---|---|---|---|---|---|---|---|---|
| TACTILE | Sphericity Assumed | 10.962 | 3 | 3.654 | 33.651 | .008 | .971 | 100.953 | .983 |
| | Greenhouse-Geisser | 10.962 | 1.000 | 10.962 | 33.651 | .109 | .971 | 33.651 | .351 |
| | Huynh-Feldt | 10.962 | . | . | . | . | .971 | . | . |
| | Lower-bound | 10.962 | 1.000 | 10.962 | 33.651 | .109 | .971 | 33.651 | .351 |
| Error (TACTILE) | Sphericity Assumed | .326 | 3 | .109 | | | | | |
| | Greenhouse-Geisser | .326 | 1.000 | .326 | | | | | |
| | Huynh-Feldt | .326 | . | . | | | | | |
| | Lower-bound | .326 | 1.000 | .326 | | | | | |

(a)Computed using alpha = .05

The data of Table 3 is likely a better representation of stuttering reality, as it reduces the between-participant stuttering severity variability; instead of allowing the different inter-personal stuttering severity to contaminate the data, we are allowing ourselves to focus on changes in stuttering frequency as a result of the treatment.

As a result, the F statistic is 33.651 (representing an increase between group variability/within-group variability), statistical significance of 0.008, and an effect size (partial eta squared) of an impressive 0.971. Even if we go for a more conservative greenhouse-geisser p-value, the data is still compelling even at such a low sample size.

The results show that the claimed device and methods are very effective in reducing stuttering across different levels of stuttering severity.

Both of the embodiments were produced as working examples to test the methods disclosed. Although only two embodiments are disclosed, the application is not intended to be limited to these embodiments. In an alternative embodiment, the devices would utilize Bluetooth wireless channels. The wireless channels would replace the wires that are used between the transducer and the processing interface and between the interface and the output vibrating device for both designs. This would enable users to more comfortably use the devices. Next, the regular batteries could be replaced with rechargeable batteries with longer battery life to add additional convenience in their operation. An output level control can also be incorporated with this design so that the level of feedback that a user gets could be adjusted based on each user. Finally, in order to significantly reduce costs, the vibrating device that is currently being used as the output device could be replaced with a much cheaper design based on modified speakers.

It is likely that the invention can be used with other disorders besides stuttering. For example, it is believed that the claimed device can be useful in alleviating symptoms associated with Parkinson's disease. Although further clinical testing may be required, the use in alleviating other symptoms is contemplated to be within the scope of this invention.

The terms "comprising," "including," and "having," as used in the claims and specification herein, shall be considered as indicating an open group that may include other elements not specified. The terms "a," "an," and the singular forms of words shall be taken to include the plural form of the same words, such that the terms mean that one or more of something is provided. The term "one" or "single" may be used to indicate that one and only one of something is intended. Similarly, other specific integer values, such as "two," may be used when a specific number of things is intended. The terms "preferably," "preferred," "prefer," "optionally," "may," and similar terms are used to indicate that an item, condition or step being referred to is an optional (not required) feature of the invention.

The invention has been described with reference to various specific and preferred embodiments and techniques. However, it should be understood that many variations and modifications may be made while remaining within the spirit and scope of the invention. It will be apparent to one of ordinary skill in the art that methods, devices, device elements, materials, procedures and techniques other than those specifically described herein can be applied to the practice of the invention as broadly disclosed herein without resort to undue experimentation. All art-known functional equivalents of methods, devices, device elements, materials, procedures and techniques described herein are intended to be encompassed by this invention. Whenever a range is disclosed, all subranges and individual values are intended to be encompassed. This invention is not to be limited by the embodiments disclosed, including any shown in the drawings or exemplified in the specification, which are given by way of example and not of limitation.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

All references throughout this application, for example patent documents including issued or granted patents or equivalents, patent application publications, and non-patent literature documents or other source material, are hereby incorporated by reference herein in their entireties, as though individually incorporated by reference, to the extent each reference is at least partially not inconsistent with the disclosure in the present application (for example, a reference that is partially inconsistent is incorporated by reference except for the partially inconsistent portion of the reference).

We claim:

1. A method for reducing the occurrence of stuttered behavior, comprising:
   a. detecting vocalization of a user; and
   b. providing a real time tactile feedback to the user, wherein said tactile feedback is not auditory feedback, and wherein said tactile feedback is continuing and corresponding to all of said detected vocalization of the user.

2. The method of claim 1 wherein the step of detecting vocalization is performed by detecting an auditory speech signal.

3. The method of claim 1 wherein the step of detecting vocalization is performed by detecting a vibrotactile speech signal.

4. The method of claim 3 wherein the vibrotactile speech signal is detected using an accelerometer.

5. The method of claim 3 wherein the vibrotactile speech signal is detected using a vibration sensing device.

6. The method of claim 1 wherein the tactile feedback is produced by a vibration producing mechanism.

7. The method of claim 6 wherein the vibration mechanism is selected from the list consisting of a skin transducer, a shaker, a speaker, and a motor.

8. A device that reduces the occurrence of stuttering, comprising:
   a. means to detect vocalization; and
   b. means to provide a real time tactile feedback, wherein said tactile feedback is not auditory feedback, and wherein said tactile feedback is continuing and corresponding to all of said detected vocalization of a user.

9. The device of claim 8 wherein the means to detect vocalization detects an auditory speech signal.

10. The device of claim 8 wherein the means to detect vocalization detects a vibrotactile speech signal.

11. The device of claim 10 wherein the vibrotactile speech signal is detected using an accelerometer or a vibration sensing device.

12. The device of claim 8 wherein the tactile feedback is produced by a vibration mechanism.

13. The device of claim 12 wherein the vibration mechanism is selected from the list consisting of a shaker, a speaker, and a motor.

14. A prosthetic device for reducing the occurrence of stuttering comprising:
   a. a vocalization detector;
   b. a filter; and
   c. a tactile feedback producer, wherein said tactile feedback producer produces a real time tactile feedback, and wherein said tactile feedback is continuing and corresponding to all of said detected vocalization of a user;
   wherein said prosthetic device is configured to not produce an auditory feedback.

15. The device of claim 14 further comprising a mechanism for activating tactile feedback at the occurrence of a silent stutter.

16. The device of claim 14 configured to be a portable device.

17. The device of claim 14 wherein the vocalization detector detects an auditory speech signal.

18. The device of claim 14 wherein the vocalization detector detects a vibrotactile speech signal.

19. The device of claim 14 wherein the vocalization detector is an accelerometer or a vibration sensing device.

20. The device of claim 14 wherein the tactile feedback producer is a vibration mechanism.

* * * * *